United States Patent [19]

Halbert et al.

[11] 4,317,810

[45] * Mar. 2, 1982

[54] WAFFLE-LIKE MATRIX FOR IMMUNOASSAY AND PREPARATION THEREOF

[75] Inventors: Seymour P. Halbert, Miami; Milton Anken, N. Miami Beach, both of Fla.

[73] Assignee: Cordis Laboratories, Inc., Miami, Fla.

[*] Notice: The portion of the term of this patent subsequent to Jun. 5, 1996, has been disclaimed.

[21] Appl. No.: 126,525

[22] Filed: Mar. 2, 1980

Related U.S. Application Data

[63] Continuation of Ser. No. 617,746, Sep. 29, 1975, abandoned.

[51] Int. Cl.$^3$ ............... G01N 31/06; G01N 33/48; G01N 33/52; G01N 33/54
[52] U.S. Cl. ................... 424/12; 23/230 B; 260/112 R; 422/50; 422/57; 422/58; 422/61; 422/68; 435/180; 435/181; 424/1; 424/1.5; 424/13; 424/78; 525/54.1
[58] Field of Search ............... 424/1, 11, 12, 13, 78; 260/6, 8, 112 R; 435/180, 181; 23/230 B; 422/50, 57, 58, 61, 68

[56] References Cited

U.S. PATENT DOCUMENTS

| | | | |
|---|---|---|---|
| 3,507,618 | 4/1970 | Murty | 424/2 X |
| 3,700,609 | 10/1972 | Tregear | 424/12 X |
| 3,853,987 | 12/1974 | Dreyer | 424/1 |
| 4,157,280 | 6/1979 | Halbert | 23/230 B |

OTHER PUBLICATIONS

Grabow, The J. of Infect. Dis., vol. 127, Feb. 1973, pp. 183–186.
Protapol DI/1, Imperial Chem. Ind., Melbourne, Australia, package flyer, 2 pp.
Bikarman, Physical Surfaces, Acd. Press, N.Y., Physical Chem. Monograph Series, vol. 20, 1970, pp. 169–193, 208–213.
British Catalogue of Plastics, The Nat. Trade Press, London, 1948, p. 109.

*Primary Examiner*—Anna P. Fagelson
*Attorney, Agent, or Firm*—Kenway & Jenney

[57] ABSTRACT

A disc-shaped insoluble matrix is formed of a polymeric material having a layer of reactive groups which react with proteins binding them covalently and uniformly to its surface. An antibody adapted for use in immunoassay of antigens associated with hepatitis is covalently bonded to the reactive groups. The matrix is provided with irregular, e.g., waffle-like, surfaces designed to increase the amount of antibody that will be in contact with a test solution such as serum.

10 Claims, 2 Drawing Figures

WAFFLE-LIKE MATRIX FOR IMMUNOASSAY AND PREPARATION THEREOF

This is a continuation, of application Ser. No. 617,746, filed Sept. 29, 1975, abandoned.

BACKGROUND OF THE INVENTION

This invention relates, in general, to insoluble reagents useful in performing immunoassays for hepatitis, and more particularly to a water insoluble polymeric disc having a layer of antibody reactive with antigens associated with hepatitis covalently bonded to a surface which is designed to increase the contact between the antibody and the antigen.

Insoluble solids used to immobilize water soluble biological substances such as proteins, enzymes, antigens, and antibodies are known. Examples of such solids may be found in U.S. Pat. No. 3,853,987 to W. J. Dreyer, U.S. Pat. No. 3,666,733 to R. Epton, and U.S. Pat. No. 3,645,852 to R. E. A. Axen et al. One use for such solids, when bonded to a suitable material, is in the detection of antigens or antibodies associated with diseases found in human blood.

Since the recent discovery of antigens associated with hepatitis, a number of procedures have been developed which are designed to detect the presence of the antigen in blood by utilizing insolubilized reagents and the well-known antigen-antibody reaction. One such process is disclosed in U.S. Pat. No. 3,867,517 entitled *Direct Radioimmunoassay for Antigens and their Antibodies*, by Chung-Mei Ling. This patent discloses a method for direct immunoassay of antigens which utilizes a coated test well, i.e., an insoluble solid, onto which the hepatitis antibody is adsorbed.

Another process for detecting hepatitis antigen is disclosed in copending U.S. patent application Ser. No. 617,743, entitled *Method of Determining the Presence of an Antigen Associated with Hepatitis*, by Seymour P. Halbert et al, filed Sept. 29, 1975, the teachings of which are incorporated herein by reference. That application discloses a sensitive, rapid technique for detecting antigens associated with hepatitis and present in body fluids. Briefly, the technique involves incubating a small sample of body fluid to be tested for antigens associated with hepatitis with an insoluble, disc-like solid matrix having an antibody reactive with hepatitis antigens bonded to its surface. If the sample contains an antigen associated with hepatitis, a bond forms between the immobilized antibody and the antigen found in the test sample. The reagent on the solid matrix is then incubated with hepatitis antibody, tagged or labeled with an enzyme capable of catalyzing a reaction of a substrate to form a detectable end product. If a hepatitis antigen was present in the test sample, a "sandwich" structure is formed comprising the insoluble matrix, hepatitis antibody, hepatitis antigen, and enzyme tagged hepatitis antibody. A third incubation, this time with a solution of suitable enzyme substrate, will indicate the presence of the antigen in the test sample since the now immobilized enzyme will catalyze the formation of an end product measurable with a photometric detector.

The ideal test for a hepatitis antigen should be easily performed, highly sensitive, rapid, capable of eliminating false positives, utilizing stable reagents and requiring only a very small sample of test body fluid. The reagents used in any hepatitis detection system should be designed as much as possible with a view of these ends.

Accordingly, it is an object of the present invention to provide an insoluble matrix useful as described in the abovementioned tests which has a high concentration of purified, hepatitis antibody distributed uniformly over its entire surface.

A further object is to attach hepatitis antibody to a solid such that it will not be dislodged by mechanical or chemical forces to which it may be subjected during use. In this regard, it is imperative to effect the attachment such that the antibody remains functional, i.e., capable of participating in its immunological reaction and immunochemically unaltered by its attachment.

A further object of the invention is to provide an improved shape for an insoluble antibody coated solid which is easy to handle during immunoassay and which is designed to expose a greater portion of its coated surface to the solutions used during incubations.

SUMMARY OF THE INVENTION

In accordance with the present invention, a disc-like insoluble member or matrix is provided which has a plurality of groups reactive with proteins grafted uniformly to its surface layer. Purified hepatitis antibody is covalently bonded to the reactive groups to provide an exterior layer of hepatitis antibody.

In the immunoassay for which the insoluble member is designed for use, the insoluble member is placed in a flat-bottomed vial and just covered with a liquid test sample. For the test to be reproducible, it is important that the antigens in the test sample be exposed to the entire surface of the antibody coated discs. It has been discovered that use of a flat or planar surfaced disc results in loss of sensitivity. Accordingly, the two opposed surfaces of the disc of the invention are distorted to an irregular configuration to reduce the disc surface-vial bottom contact. In one preferred embodiment, the opposed surfaces are rendered waffle-like by passing the disc through a press prior to attachment of the antibody.

DESCRIPTION OF THE PREFERRED EMBODIMENT

U.S. Pat. No. 3,700,609 entitled *Graft Copolymers*, to G. W. Tregear et al., the disclosure of which is incorporated herein by reference, discloses an insoluble continuous polymeric substance comprising a polymeric backbone onto which side chains of another polymer or copolymer are grafted. By suitable choice of the grafted polymer, it is possible to chemically link biological substances to the insoluble substrate. A product which is disclosed in the above patent is commercially available in a disc form under the tradename PROTAPOL DI/1 from Imperical Chemical Industries of Australia and New Zealand (ICIANZ).

The PROTAPOL DI/1 comprises a polytetrafluoroethylene backbone having isothiocyanopolystyrene groups grafted uniformly over its surface and is designed for use in radioimmunoassay. The discs, as presently available, are approximately 0.01 inches thick and 0.5 inch in diameter.

Figure 1:
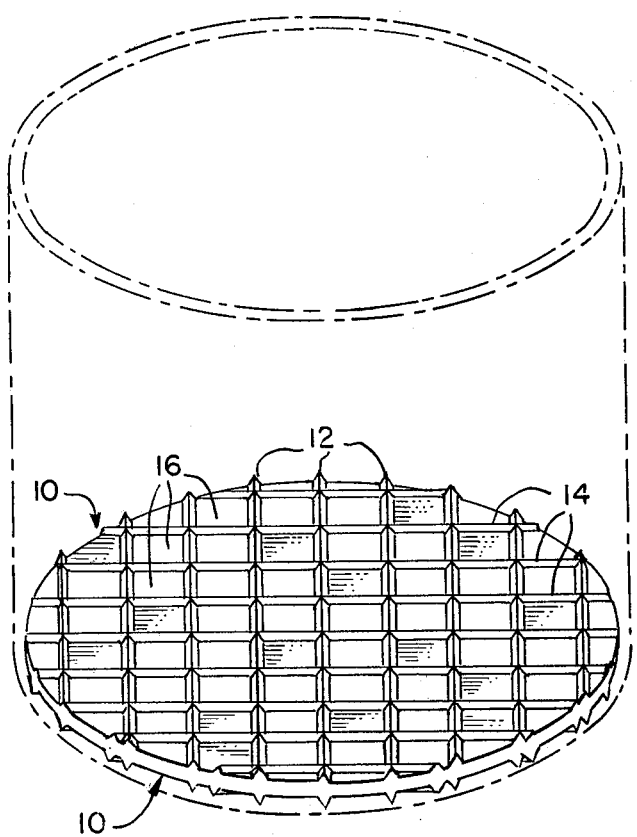
FIG. 1 is a perspective view of a disc embodying features of the invention in a vial; and, FIG. 2 is a cross-section view of the disc of FIG. 1.
Figure 2:
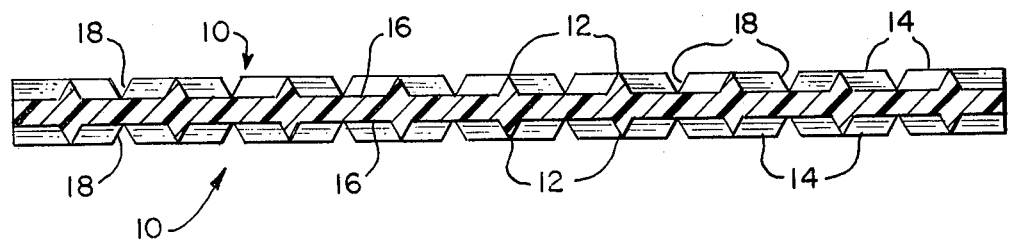

In accordance with one important embodiment of the present invention, each disc is provided with a waffle-like pair of surfaces 10 comprising a first series of linear ridges 12 and a second series of linear ridges 14 which form grids. Ridges 12 and 14 are preferably perpendicular to each other and hence define a plurality of square depressions 16. As seen in FIG. 2, the sides of each ridge 12 and 14 taper upwardly from adjacent pairs of depression 16 to form a line defining the top of the ridge. It should be noted that in order to facilitate the description of the invention, the ridges 12 and 14 are greatly exaggerated in the drawing.

The desired configuration of the disc is achieved by passing the disc through rollers having projections on the surface of the rollers designed to impart the desired configuration on the disc. As is obvious, the rollers are designed to provide a sufficient amount of pressure to disfigure the polymeric material in the disc without actually puncturing the disc. This fact is important because it should be noted that the disc has a reactive layer on its surface. Thus, penetration of the disc would expose the teflon to which no antibody can be bonded. Exposure of the teflon layer would actually result in a disc which would have a lower bonding capacity.

The main consideration is to provide a disc matrix with surfaces which, when placed in a flat bottomed vial, will be substantially in complete contact with the test sample, i.e., there should be a minimum of surface-to-surface contact between the matrix and the bottom of the vial. In another important embodiment of the invention, the disc is configured to have a field of high points and low points.

The hepatitis antibody which is to be attached to this insoluble solid is preferably prepared as disclosed in copending U.S. patent application U.S. Ser. No. 671,744, filed Sept. 29, 1975, entitled *Enzyme Tagged Hepatitis Associated Antibody*, by Seymour P. Halbert et al., filed Sept. 29, 1975, the disclosure of which is incorporated herein by reference. This purified hepatitis antibody must be attached to the disc such that its immuno-reactive groups remain accessible, and its activity is not altered by the attachment process.

The antibody, which typically has been preserved in the lyophilized state, is reconstituted by adding 100 ml of 0.1 M $NaHCO_3$ (pH 9.6) for each 5.0 mg of antibody. In general, the procedure for attachment involves contacting 1000 waffled discs with the dilute solution at 2°–8° C. for 8 to 16 hours, with agitation. Afterwards, the antibody solution is discarded and the discs are washed twice with successive volumes of 0.1 M $NaHCO_3$, pH 9.6, phosphate buffered saline, and cold (2°–8° C.) 0.3% bovine serum albumin in phosphate buffered saline with 0.5% TWEEN 20. After an additional washing with crystalline bovine serum albumin, and freezing e.g. over dry ice, lyophilization is carried out and the discs are stored at 2°–8° C. until ready for use.

Although the description in this specification relates to the preparation of discs having hepatitis antibody bonded thereto, it should be apparent to those skilled in the art that the disc of the present invention is useful to immobilize an almost limitless number of proteins. For example, the increased contact between the test sample and the disc enables the disc to be used in tests which involve the bonding of the following proteins thereto: antibodies to drugs such as digoxin, opiates, steriods; antibodies to natural products, for example insulin and other hormones; and, specific enzymes to metabolites found in blood and other body fluids.

EXAMPLE

The following procedure was used to prepare 8,000 discs, each of which were first treated with the press to produce the desired configuration as described. A batch of 8,000 discs requires 40 mg of hepatitis antibody, i.e., 5 mg per 1,000 discs. The protein content of the reconstituted hepatitis antibody is adjusted to 0.05 mg/ml in a final volume of 800 ml in 0.1 M $NaHCO_3$ (pH=9.6). The entire 800 ml of buffered antibody is then added to a 1,000 ml screw-cap bottle provided with a leak proof liner containing the 8,000 discs, and the bottle is rotated for 16 hours, e.g., overnight, at 2°–8° C. to slowly tumble the discs through each rotation cycle. Afterwards, the liquid is poured from the bottle and discarded and the discs are transferred to a wide-mouth 2 liter flask.

The discs are washed twice with successive 1 liter volumes of cold (2°–8° C.) 0.1 M $NaHCO_3$ pH 9.6, following which the buffer is removed. The discs are then washed again, this time using two successive 1 liter volumes of cold buffer (0.01 M sodium phosphate, 0.15 M NaCl, pH=7.4). After removing residual buffer, the discs are washed for a third time, using two successive one liter volumes of cold bovine serum albumin solution (0.3%).

The discs are finally washed with two successive 1 liter volumes of a solution of cold crystalline bovine serum albumin (pH=8) at a concentration of 2 mg/ml. This step is performed to provide a protein environment for the protein on the disc. The discs, after removing the residual wash, are then transferred to dishes or trays (9"×9"), each of which is lined with a sheet of filter paper and each of which contains 200 ml of the crystalline bovine serum albumin solution. When the transfer is complete, a sheet of filter paper is used to cover them. Buffer is thoroughly removed. The discs are then quick frozen for 30 minutes on dry ice.

The contents of the tray are then lyophilized. The dry discs are then removed and stored in stoppered containers.

In operation, the discs are used as an insoluble reagent during immunoassay of hepatitis associated antigen as disclosed, for example, in the aforementioned copending U.S. application Ser. No. 617,743. Briefly, a series of vials are set out in a rack and each is labeled to correspond to a test sample identification. A 0.05 ml sample of horse globulin solution and a 0.5 ml aliquot of test sample or a positive or negative control serum and one of the antibody coated disc of the invention are added together in each vial. The contents of the vials are then incubated at 43° C. for 0.5 hours in, for example, a water bath. Moderate shaking ensures that intimate contact between the antigen present in the test samples and the discs occurs. The waffle-like surfaces of the discs enhance this process by ensuring that both the top and the bottom antigen coated surfaces are exposed to the test samples. An immunochemical bond forms between the immobilized antibody and antigens present in the sample.

After the first incubation is complete, the supernatant is aspirated from each vial and the contents of the vials are washed to remove any unbonded antigen. A 0.3 ml sample of enzyme-tagged antibody reagent is then added to each vial and incubated for one hour at 43° C. with continuous moderate shaking. For further details see copending application Ser. No. 617,744, abandoned, entitled *Enzyme Tagged Hepatitis Associated Antibody*, filed Sept. 29, 1975, the teachings of which are incorporated herein by reference. During the second incubation, the enzyme tagged antibody reacts with antigens that were fixed to the antibody coating on the disc of the invention during the first incubation. Thus, a "sandwich" is formed consisting of the disc, antibody, hepatitis associated antigen, and enzyme-tagged antibody.

After the second incubation, the supernatants are aspirated as before and the disc in each vial is washed to remove any unbonded enzyme-tagged antibody. The discs are then transferred into clean vials and a 2.5 ml aliquot of enzyme substrate solution containing 1 mg/ml of the enzyme substrate is added to each vial. A third incubation for 1 hour at 43° C., with continuous shaking, effects a chemical change in the substrate which occurs only if the enzyme is immobilized on the disc, i.e., only if antigen was present in the sample and a "sandwich" formed.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A material for use in immunoassay comprising a water insoluble polymeric matrix having a layer of reactive groups grafted into its surface, said reactive groups being capable of covalently bonding to protein to enable the structure to be used in immunoassay wherein the improvement comprises a designed configuration of top and bottom waffle-like surfaces having a plurality of ridges and depressions on said polymeric matrix which, when placed in a flat bottom vial, both top and bottom surfaces will be substantially in contact with any solution in the vial while minimizing the surface to surface contact between the matrix and the bottom of the vial.

2. The material as set forth in claim 1 wherein an antibody reactive with antigens associated with hepatitis is covalently bonded to the reactive groups on said polymeric matrix.

3. The material of claim 1 wherein waffle-like surfaces include a series of linear parallel ridges.

4. A material in accordance with claim 3 wherein both waffle-like surfaces include a first series of linear ridges and a second series of linear ridges arranged perpendicular to said first series of linear ridges.

5. The material of claim 1 wherein said waffle-like surfaces are formed by passing the polymeric matrix through a pair of rollers having surface projections of a design to impart the waffle-like surface configuration onto the polymeric matrix by pressing.

6. A method for producing a material useful in immunoassay comprising:
(a) providing a disc shaped polymeric matrix which has groups reactive with proteins grafted onto its opposed surfaces;
(b) distorting the opposed surfaces on said reactive groups with a designed configuration in the form of a plurality of ridges and depressions without puncturing the disc so that when said matrix is placed in the bottom of a vial both surfaces will be substantially in complete contact with any solution in the vial and there will be a minimum of surface-to-surface contact between the matrix and the bottom of the vial;
(c) covalently bonding a protein onto the reactive groups to enable the material to be utilized in assaying the presence of material which react with the bound protein.

7. The method as set forth in claim 6 wherein in step (c) an antibody reactive with antigens associated with hepatitis is covalently bonded to the reactive groups on said polymeric matrix.

8. The method as set forth in claim 6 wherein in step (b) said surfaces are distorted to have a waffle-like configuration.

9. The method as set forth in claim 8 wherein said waffle-like configuration is formed by passing the matrix between the surfaces of two rollers to press the configuration into the polymeric matrix.

10. The method as set forth in claim 9 wherein in step (c) an antibody reactive with antigens associated with hepatitis is covalently bonded to the reactive groups on said polymeric matrix.

* * * * *